United States Patent [19]

Otto

[11] 4,038,301
[45] July 26, 1977

[54] REMOVAL AND RECOVERY OF ORGANOLEAD COMPOUNDS FROM ACTIVATED CARBON AND RECOVERY OF THE ACTIVATED CARBON

[75] Inventor: Jack M. Otto, Beaumont, Tex.

[73] Assignee: PPG Industries, Inc., Pittsburgh, Pa.

[21] Appl. No.: 630,839

[22] Filed: Nov. 10, 1975

[51] Int. Cl.$^2$ .............................................. C07F 7/24
[52] U.S. Cl. .................................. 260/437 R; 252/413
[58] Field of Search ...................... 260/437 R; 252/413

[56] References Cited

U.S. PATENT DOCUMENTS

| | | | |
|---|---|---|---|
| 1,533,031 | 4/1925 | Sauer et al. | 252/413 |
| 2,407,262 | 9/1946 | Linch | 260/437 R |
| 2,704,281 | 3/1955 | Appell | 252/413 |
| 2,763,673 | 9/1956 | Gittins | 260/437 R |
| 2,851,352 | 9/1958 | Erickson | 75/115 |
| 2,867,497 | 1/1959 | Houdry et al. | 252/413 |
| 3,082,059 | 3/1963 | Goren | 252/413 X |
| 3,112,277 | 11/1963 | Michalko | 252/413 |
| 3,117,936 | 1/1964 | Michalko | 252/413 |
| 3,452,069 | 6/1969 | Cliver | 260/437 R |
| 3,720,626 | 3/1973 | Benzarin | 252/413 |

*Primary Examiner*—Helen M. S. Sneed
*Attorney, Agent, or Firm*—Richard M. Goldman

[57] ABSTRACT

Disclosed is a method of recovering organolead compounds from solid porous activated carbonaceous materials. According to the disclosed method, an activated carbonaceous material having organolead compounds deposited therein is contacted with an extracting solution of a strong acid or base and an organolead compound bearing aqueous composition solution is recovered. The disclosed method may be used for recovering organolead compounds from aqueous solutions by first contacting the aqueous solution with a solid, activated, carbonaceous material, to thereby deposit the organolead compound on the solid activated carbonaceous material. Thereafter, the organolead compound containing solid activated carbonaceous material is contacted with the aqueous solution of the strongly ionized material to recover an organolead compound bearing aqueous composition. The method may also be used to render the carbonaceous material useful for further removal of lead.

7 Claims, No Drawings

REMOVAL AND RECOVERY OF ORGANOLEAD COMPOUNDS FROM ACTIVATED CARBON AND RECOVERY OF THE ACTIVATED CARBON

DESCRIPTION OF THE INVENTION

In the production of alkyl lead compounds, especially tetraethyl lead automotive anti-knock compounds, a sodium lead alloy and ethyl chloride are reacted in an autoclave. The products of the autoclave include solids, liquids, and gases, such as sodium chloride, ethane, ethyl choride, chlorinated hydrocarbons, lead alkyl, lead alkyl complexes, and the like. The autoclave product is distilled in a steam still to separate the stream into individual products. The solid fraction contains lead while the liquid fraction contains tetraethyl lead and automotive anti-knock compounds.

At other stages of the automotive anti-knock compound production process, the reactants, intermediates, and products are contacted with large quantities of water. The water from these various intermediate processes, as well as products from the steam still, contains water soluble organolead compounds. These organolead compound bearing aqueous streams may be treated by various primary treatment techniques, such as collection and storage in clarifying tanks and settling lagoons or filtration and thereafter subjected to secondary treatment techniques such as sequestrants and precipitants to convert the lead to essentially insoluble inorganic divalent lead compounds.

However, the treated water from these prior purification steps still contains from about 1 to about 200 parts per million of lead and, most frequently, from about 1 to about 20 parts per million of lead. This lead is in the form of organic compounds of Pb(+4) and cannot be readily precipitated or otherwise easily removed. The organolead compounds may, however, be recovered by various tertiary treatment methods including electrolysis, complexing agents, further sequestrants, and pH control among others. One such process is adsorption of the organolead compounds onto a bed of activated carbon, such as by passing the liquid composition through the bed of activated carbon and recovering a liquid composition substantially reduced in organolead compound concentration.

One form of activated carbon particularly useful in carrying out the adsorption of organolead compounds is an activated carbon having a porosity of from about 0.30 to about 0.85, and preferably from about 0.80 to about 0.85, a mean pore diameter of from about 3 to about 100 Angstroms and preferably from about 15 to about 50 Angstroms, a mean particle diameter from about 0.1 to about 10 millimeters, and preferably from about 0.4 to 1.0 millimeter, and a means specific area of from about 500 to about 1600 square meters per gram, and preferably from about 800 to about 1500 square meters per gram. The activated carbon is further characterized by a bulk dry density of from about 22 to about 37 pounds per cubic foot, preferably from about 25 to about 35 pounds per cubic foot.

According to the method disclosed herein, the adsorbed organolead compounds may be desorbed from the activated carbon and recovered in a more concentrated form by contacting the activated carbon with an aqueous extracting solution, i.e., a solution of a strongly ionized material, and recovering an aqueous composition containing desorbed inorganic compounds therein.

DETAILED DESCRIPTION OF THE INVENTION

According to the method disclosed herein, organolead compounds may be removed from carbonaceous solids, such as activated carbon and activated charcoal, by contacting the organolead compound bearing carbonaceous solids with an aqueous extracting solution, i.e., an aqueous solution of a strongly ionized material, e.g., a strong acid or a strong base. This method may be used to remove the organolead compounds from carbonaceous solids by contacting the organolead containing carbonaceous solid with a dilute mineral acid such as dilute hydrochloric acid, sulfuric acid, or nitric acid, or a dilute base such as potassium hydroxide or sodium hydroxide, and subsequently recovering therefrom a dilute solution of enhanced inorganic compound concentration. The method of this invention may also be used to recover the organolead compounds absorbed on solid carbonaceous solids, such as activated carbon and activated charcoal, by contacting the organolead compound bearing activated carbon with the dilute aqueous solution, withdrawing an aqueous solution of higher organolead content, and subsequently precipitating the lead from the extracting solution, e.g., by adjusting the pH into the strongly basic range, for example, above about 9.5.

The method of this invention may also be used to remove organolead compounds from dilute aqueous solutions by passing the dilute solution through a bed of solid, carbonaceous material, such as activated carbon or activated charcoal, and recovering a solution diminished in organolead compounds. Thereafter, for example, prior to or when breakthrough occurs, a dilute aqueous extracting solution of hydrochloric acid may be passed through the bed of activated carbonaceous material to remove the organolead compounds adsorbed on the carbonaceous material.

The aqueous solvent or extracting solutions useful in the method of this invention are aqueous solutions of strong acids and aqueous solutions of strong bases.

By a strong acid is meant an acid having a negative $pk_a$ or acid constant where the $pk_a$ or acid constant is defined as;

$$pk_a = -\log\left[\frac{(H^+)(A^-)}{(HA)}\right]$$

for the equilibrium;

$$HA \rightleftharpoons H^+ + A^-$$

For strong mineral acids useful in the method of this invention, such as $HNO_3$, $H_2SO_4$, $HClO_4$, $HMnO_4$, $HCl$, $HBr$, and $HI$, the $pk_a$ at 27° C. is negative, and frequently as high as $-6$ or $-7$. Such acids are characterized as being almost completely or substantially ionized in water.

By a strong base is meant a base that is completely or substantially ionized in water. Such bases include KOH and NaOH.

According to the method of this invention, activated charcoal or activated carbon having organolead compounds adsorbed thereon is contacted with aqueous extracting solution. The concentration and temperature of the aqueous extracting solution, the residence time of the extraction solution in the carbon bed, the direction of flow of extracting solution, and the quantity of extracting solution used, that is, the ratio of the volume of extracting solution to the volume of the bed, are interrelated. For example, when the extracting solution is aqueous hydrochloric acid, the method of this invention may be carried out at temperatures from the freezing point of the dilute hydrochloric acid solution, e.g., from a lower limit between $-5°$ to $0°$ C., to the boiling point of the hydrochloric acid solution, e.g., to an upper limit of from about 90° to 100° C. at one atmosphere and to higher temperature under elevated pressures. Generally, the temperature is from about 0° to about 95° C., and preferably from about 15° to about 75° C. As a practical matter, the temperature will be from about 25° to about 60° C.

At temperatures of from about 25° to about 60° C. the concentration of the aqueous extracting solution is from about 0.1 normal to about 5 normal. Generally, the solution is from about 0.5 normal to about 2.0 normal. Preferably, the solution is about 1 normal, that is, about 3.7 weight percent for hydrochloric acid. The actual concentration of the ionizable material is determined by economic factors including the availability of the acid or base, pumping capacity, storage capacity, treating capacity, and the like. The residence time, that is, the ratio of the volume of the carbon bed to the volumetric flow rate of the acid, where the volume of the bed is defined by the ratio $$V = \frac{M}{\rho(1-\epsilon)}$$

where $V$ is the volume of the bed, $M$ is the total mass of the bed, $\rho$ is the density of the individual activated carbon particle, and $\epsilon$ is the porosity of the bed, is from about 1 minute to about 250 minutes and preferably from about 5 minutes to about 50 minutes for 0.5 to 1.5 normal solutions at 25° to 60° C. Particularly preferred are residence times ranging from about 10 to about 25 minutes.

The ratio of volume of extracting solution to the volume of the bed depends upon the condition, history, and porosity of the bed, and the temperature, residence time, and strength of the solution. For example, for the passage of 0.5 to 1.5 normal aqueous hydrochloric acid through a bed containing about 1.0 to about 2.0 percent adsorbed organolead compounds at a residence time of from 5 to 50 minutes, and a temperature of from 25° to 60° C., and a bed that has only been used once or twice, satisfactory results are obtained with from 20 to 50 volumes of acid per volume of bed, and preferably with less than 50 volumes of aqueous hydrochloric acid per volume of the bed. However, lead species are recovered from the carbon when only small amounts, e.g., 1 volume or less, of hydrochloric acid are used.

The aqueous extracting solution may flow upward through the bed, for example, upward through a vertically disposed bed by being pumped in a direction counter to the flow of gravity. Alternatively, the aqueous hdyrochloric acid may be allowed to flow downward through the bed, for example, under the influence of gravity. Particularly good results are obtained if the aqueous extracting solution is pumped upward through the bed, i.e., pumped in a direction counter to the force of gravity. Particularly good results may also be obtained if the aqueous extracting solution is pumped downward through the bed at a higher flow rate than would be encountered in gravity flow. It is believed that this causes some turbulence of the aqueous extracting solution, resulting in better contact of the carbon particles by the extracting solution.

Thereafter, the aqueous extracting solution, increased in organolead content, is recovered. Typically, when the extracting solution is aqueous hydrochloric acid, after passage through the bed, the organolead compound content of the aqueous hydrochloric acid is in the range of at least about 50 milligrams per liter. The organolead concentration may, however, be as high as 100 or even 500 milligrams per liter.

After passing the aqueous extracting solution through the bed and recovering an aqueous solution of enhanced organolead compound concentration and neutralizing the pH of the bed, e.g., to above about pH6, and preferably between pH6 and pH8, the flow of organolead compound containing material, such as clarifier overflow, may be resumed through the bed of activated carbon.

The lead may be recovered from an acid solution as a sulfuric acid, phosphoric acid, nitric acid, hydrochloric acid solution by adjusting the pH of the organolead containing hydrochloric solution to above about 9.5, e.g., from about 9.5 to 10.5 or higher. This may be accomplished by adding a basic material such as potassium hydroxide, sodium hydroxide, or even sodium chloride-sodium hydroxide to the solution. Adjustment of the pH in this way serves to precipitate the lead.

The water soluble organolead compounds normally recovered by the method of this process are organic compounds of Pb(+4), as exemplified by organolead halides, most frequently organolead chlorides having the formula;

$$PbR_{4-x}Cl_x$$

where R is an aryl group or alkyl group having from 1 to 8 carbon atoms and most frequently an alkyl group having from 1 to 3 carbon atoms, and $x$ is a number from 1 to 3, generally from 1 to 2. Most commonly, R is a methyl group, $CH_3$, or the ethyl group, $CH_2CH_3$, although it may be a propyl group, butyl group, a pentyl group, a hexyl group, an octyl group, or an aryl group. The R's may all be the same group or they may be different groups. Additionally, some tetraethyl lead or tetramethyl lead may also be present in the solution and recovered by the method herein described.

The most common water soluble organolead compound by-products of the lead alkyl automotive antiknock compound production processes are triethyl lead chloride, diethyl lead dichloride, ethyl lead trichloride, trimethyl lead chloride, dimethyl lead dichloride, and methyl lead trichloride. Most commonly, the principle water soluble organolead compound is triethyl lead chloride. Additionally, tetraethyl lead may be dispersed in the liquid composition. Such tetraethyl lead is normally removable by filtration.

The concentration of organolead compounds in the solutions fed to the activated carbon bed, e.g., clarifier pond and settling lagoon overflows, is most frequently at trace levels, i.e., well below the concentrations at which the relatively insoluble organolead compounds and the reaction products thereof precipitate out of solution. The overflow from clarifier ponds and settling lagoons contains less than 2,000 parts per million of organolead compounds and, typically, less than 200 parts per million of the organolead compounds. Most frequently, the solutions contain less than about 100 parts per million of organolead compounds. As a practical matter, the overflow from clarifier ponds and settling lagoons contains from about 1 to about 20 parts per million of these compounds. Most commonly, the organolead compounds are alkyl lead chlorides, as described above. Additionally, the overflow from clarifier ponds and settling lagoons contains about 20 grams per liter of chlorine as chlorides and hypochlorites such as sodium chloride and sodium hypochlorite. The overflows also contain small amounts of aluminum and chromium ions at the 10 to 15 parts per million level. These streams are passed through the activated carbon bed and the lead content of the streams reduced thereby.

The activated carbon is typically in the form of small particles, for example, 100 percent passing 8 mesh and substantially none passing 40 mesh, and preferably 100 percent passing 8 mesh and substantially none passing 30 mesh, although particles as large as 10.0 millimeters in diameter may be present.

Prior to contact with organolead compound bearing solutions, the specific surface area of the activated carbon useful in the method of this invention is from about 500 square meters per gram to 1600 square meters per gram and preferably from about 800 to about 1500 square meters per gram. The iodine number of activated carbon useful in the method of this invention, a measure of the total specific area is typically from about 800 to about 1200 or even 1500 and preferably above about 850 and most frequently between about 900 and 1100.

The molasses number of the activated carbon useful in the method of this invention, a measure of the large pores, i.e., the pores greater than about 28 Angstroms, is generally in the range from about 200 to 260 and most frequently in the range from about 210 to 250. The mean particle diameter of the activated carbon useful in the method of this invention is generally from about 0.1 millimeter to about 10 millimeters and most frequently in the range of from about 0.4 millimeter to about 1.0 millimeter. The porosity of the carbon bed is from about 0.30 to about 0.85 and generally in the range of from about 0.8 to about 0.85.

The activated carbon referred to herein may typically be manufactured from such carbonaceous materials as coconut shells, nut shells, coal, cereals, beans, corn cobs, cotton and cottonseed waste, distillery wastes, abattoir wastes, fruit pits, kelp, lampblack, lignin, lignite, brown sugar and molasses, peat, petroleum acid sludge, petroleum coke, potassium ferrous cyanide residues, pulp mill waste, sawdust, and wood. The carbon may be activated by gaseous oxidation or chemical activation. In gaseous oxidation, carbonization of the material occurs by destructive distillation, followed by crushing, bonding with tar or pitch, extrusion or forming, and thereafter heating to a temperature above 400° C. and preferably from about 600° to about 800° C. in an atmosphere of steam, carbon dioxide, or flue gas. This leaves a structure of relatively pure carbon.

In chemical activation, the raw material is impregnated with strong solution of an activating agent, such as zinc chloride, phosphoric acid, boric acid, calcium hydroxide, calcium chloride, calcium phosphate, chlorine, cyanides, dolomite, ferric chloride, manganese chloride, manganese dioxide, manganese sulfate, nitric acid, potassium carbonate, potassium sulfide, potassium thiocyanate, sodium hydroxide, sodium phosphate, sodium sulfate, sulfur, sulfur dioxide, or sulfuric acid. Preferably, zinc chloride or phosphoric acid is used. The water is driven off by heating and the material is calcined, degrading the organic material and leaving a porous structure of relatively pure carbon. The activating compound is then removed from the activated carbon by final washing with acid and water.

According to the method of this invention, organolead compounds are recovered from dilute aqueous solution by passing the aqueous solution through a bed of activated carbon. Typically, the organolead compound bearing aqueous solution is passed downward through a vertical bed of activated carbon in the direction of gravity flow. The dilute aqueous solution fed to the carbon bed contains from about 1 part per million up to 10 or even 20 parts per million of water soluble organolead compounds. The effluent from the packed bed contains a reduced concentration of organolead compounds and will typically contain from about 0.1 part per million of organolead compound to about 1 part per million of the organolead compounds. Most frequently, the effluent recovered from the packed bed will contain about 0.3 to about 0.8 parts per million of the water soluble organolead compounds. The flow rate, expressed as mass per unit time of the organolead compound bearing dilute solution through the bed is from about 3 to about 10 gallons per minute per square foot of cross sectional area perpendicular to the direction of flow and preferably from about 3.5 to about 8.5 gallons per square foot of bed cross sectional area perpendicular to the direction of flow. Such flow rates provide a residence time of from about 6 to about 50 minutes in a packed bed having a height of from about 9 to about 15 feet and preferably a residence time of about 10 to about 40 minutes.

The activated carbon adsorbs lead from the organolead compound bearing aqueous liquid solution until the lead adsorbed on the surface of the activated carbon is substantially in equilibrium with the lead in the solution entering the packed bed. This condition is referred to as an equilibrium amount of lead and no further lead can be adsorbed. At this point breakthrough will occur, that is, the effluent from the bed will still be rich in organolead content. Generally, the used carbon will contain from about 1.4 to about 2.5 weight percent adsorbed organolead compounds although it may contain as little as about 0.1 weight percent or as much as 6 weight percent.

When breakthrough occurs, or prior to breakthrough, when the adsorption rate begins to decline, the flow of the organolead compound bearing solution is terminated and the recovery of the adsorbed lead species, as described hereinabove, is commenced.

According to the method of this invention, the used carbon, i.e., the carbon of diminished lead adsorbing capability, containing from about 1 to about 6 weight percent lead adsorbed therein, is contacted with an aqueous extracting solution to remove the organolead compounds from the carbon, and an extracting solution of enhanced organolead content is withdrawn from contact with the carbon. Thereafter, the pH of the carbon may be adjusted to from about pH 6 to about pH 8, i.e., the carbon may be contacted with a solution until the pH of the solution withdrawn from contact with the carbon is from about pH 6 to about pH 8. Thereafter, the flow of the organolead compound bearing solution may be resumed through the carbon.

According to a further exemplification of this invention after passage of the extracting solution through the activated carbon bed, the activated carbon may be regenerated. That is, after removal of the adsorbed organolead compounds from the activated carbon, the activated carbon may be suitably treated to enhance the adsorptive capacity of the carbon and preferably to restore the adsorptive capacity thereof to the adsorptive capacity of unused activated carbon. This may be accomplished by heating the carbon to an elevated regeneration temperature and passing a regeneration material therethrough. Typically, when the regeneration material is steam, a regeneration temperature in excess of 400° C. and preferably about 600° C. is preferred. The regeneration temperature may be high as 800° C. or even 1000° C. without adverse effects. The regeneration may be carried out for from about 2 hours to 24 or even 48 hours, although a regeneration time of from about 4 to about 12 hours is preferred. Thereafter, the flow of the organolead compound bearing solution may be resumed.

The following examples are illustrative of the method of this invention.

EXAMPLE I

An aqueous solution containing between 7.0 and 8.1 milligrams of organolead compound per liter was passed through a bed of activated charcoal and reduced in lead content. Thereafter, the organolead deposited on the carbon was removed by passing aqueous hydrochloric acid upward through the carbon bed and recovering an aqueous hydrochloric acid solution of enhanced organolead compound content. Thereafter, the bed was neutralized to a pH of 7 and the flow of the aqueous composition containing from about 7.0 to about 8.1 milligrams per liter of organolead compound was resumed.

The carbon bed was in a one centimeter diameter by 24 centimeter long vertical glass tube and was 10 grams of Calgon "Filtrasorb 400" activated carbon. The activated carbon was +12 −40 mesh with a specific surface area of 1100 to 1200 square meters per gram, an iodine number of about 1000 and molasses number of 250, a bed porosity of about 0.85 and a mean particle diameter of about 0.5 millimeter.

The organolead bearing liquid composition contained the following materials:
 organolead halides—7l.1–8.0 milligrams per liter
 sodium chloride—35 grams per liter The principal organolead halides were triethyl lead chloride, diethyl lead dichloride, and ethyl lead trichloride.

Initially, the activated charcoal had no lead species adsorbed therein. The organolead compound bearing aqueous solution was passed downward through the bed at a rate of 10 milliliters per minute, providing a residence time of 1.88 minutes. Flow was continued for 18 hours and 20 minutes, and, based on analyses of the feed and effluent, approximately 90 percent of the lead was adsorbed onto the carbon.

At this point the flow of the organolead compound bearing aqueous solution was stopped and an aqueous solution containing about 1 percent aqueous hydrochloric acid at a temperature of between 48° and 51° C. was pumped upward through the bed at a flow rate of 2 milliliters per minute for 3 hours and 45 minutes. Analysis of the effluent of the aqueous hydrochloric acid treatment showed that approximately 62 percent of the calculated amount of adsorbed lead was recovered in the hydrochloric acid stream. Thereafter, the substantially lead-free effluent from the adsorption step was pumped through the bed for approximately 8 hours until the pH of discharge from the bed was 7.0.

The flow of the organolead compound bearing solution through the bed was then resumed at a flow rate of 10 milliliters per minute for 18 hours and 20 minutes. Based on the analysis of the feed to the packed bed and the effluent therefrom, approximately 82 percent of the lead in the organolead compound bearing solution was adsorbed on the lead, and the lead content of the carbon was calculated to be 1.08 weight percent. A 1.0 percent aqueous solution of hydrochloric acid at a temperature of 48° to 51° C. was then pumped upward through the bed at a flow rate of 2 milliliters per minute for 6 hours and 15 minutes. Analysis of the organolead compound containing hydrochloric acid effluent showed that 73 weight percent of the calculated amount of lead deposited on the activated carbon was recovered. The flow of hydrochloric acid was stopped and a pH of the bed was adjusted to pH 7 by passing a 4 percent aqueous solution of sodium chloride adjusted to pH 9.2 through the bed for 48 hours.

Thereafter, the flow of the organolead compound bearing aqueous solution through the bed was resumed. Based on analyses of the feed and the effluent of the bed, 80 percent of the organolead compound in the solution was adsorbed on the carbon. After 18 hours and 20 minutes of flow at a feed rate of 10 milliliters per minute, the feed was stopped and a 1 weight percent solution of aqueous hydrochloric acid with a temperature of 48° to 51° C. was pumped upward through the bed at a feed rate of 2 milliliters per minute for 7 hours and 15 minutes. During this time, approximately 73 weight percent of the calculated amount of lead adsorbed on the activated carbon was recovered in the aqueous hydrochloric acid solution. Thereafter, the flow of aqueous hydrochloric acid was stopped and the pH of the bed was adjusted by passing the aqueous solution from which the organolead compound had previously been removed upward through the bed at a flow rate of 2 milliliters per minute for 9 hours and 25 minutes.

Thereafter, the flow of the organolead compound containing aqueous composition was continued downward through the packed bed at a flow rate of 10 milliliters per minute for 18 hours and 20 minutes. During this time, based on analyses of the flow and the effluent, approximately 73 percent of the organolead compound in the solution was adsorbed onto the activated carbon. The flow of organolead compound bearing solution was then stopped and a one weight percent aqueous solution of hydrochloric acid at a temperature of 48° to 51° C was pumped upward through the bed at a flow rate of 2 milliliters per minute for 19 hours. The amount of lead recovered was in excess of the amount calculated to have been adsorbed on the carbon during the preceding adsorption cycles. The excess was presumed to arise from lead left behind by previous cycles. Thereafter, the pH was adjusted by passing effluent from which the lead had been recovered upward through the packed bed for 20 hours.

EXAMPLE II

Organolead chloride compounds were removed from activated carbon by treatment with aqueous nitric acid and subsequent bearing. A series of tests were run to determine the effect of the moles of nitric acid to calculated moles of adsorbed organolead and contact time on removal of adsorbed lead. Thereafter, a series of tests were run to determine the effect of regeneration time and temperature on percent regeneration.

Ten grams of activated carbon particles containing 2.51 weight percent adsorbed organolead chloride compounds were placed in 50.0 milliliters of distilled water. Sufficient concentrated nitric acid, one part by volume of nitric acid per part by volume of water, was added to the composition of carbon in water to obtain the specified mole ratio of nitric acid to lead, and the resulting composition was stirred for the specified times. The carbon was then washed with distilled water until no charge in pH was observed.

The results obtained are shown in Table I below. Lead removal was determined by analysis of the carbon.

TABLE I

Removal of Adsorbed Lead on Activated Carbon by Washing in $HNO_3$

| Mole Ratio $HNO_3/Pb^{+4}$ | Time Hours | Lead Removal Percent |
|---|---|---|
| 1 | 1.0 | 19.92 |
| 1 | 3.5 | 17.93 |
| 1 | 6.0 | 41.83, 45.02 |
| 50 | 1.0 | 88.45 |
| 50 | 3.5 | 79.28, 80.88, 82.07 |
| 50 | 6.0 | 83.27 |
| 100 | 1.0 | 90.84, 91.63 |
| 100 | 3.5 | 94.82 |
| 100 | 6.0 | 94.82 |

Thereafter, a series of tests were conducted to determine the effect of regeneration time and temperature on $HNO_3$ washed lead. In each test, the activated carbon particles containing 2.51 weight percent adsorbed organolead compounds were placed in 50.0 milliliters of distilled water and sufficient nitric acid to remove 95 percent of the adsorbed carbon. Thereafter, the carbon was washed with distilled water until the pH remained constant. Then the carbon particles were placed in a 1 inch outside diameter Vylor tube that was heated to a specified temperature in a tube furnace as steam was passed through the tube. This was continued for a specified time. The carbon was then tested by adding 2.0 grams of the carbon to a test solution containing in excess of 80 milligrams per liter of organolead chlorides. Percent regeneration was then calculated by comparing the first and last analysis of each experiment. The results are shown in Table II.

TABLE II

Thermal Regeneration of Spent Carbon: Effect of Time and Temperature on the Extent of Regeneration

| Time (Hours) | Temperature (° C.) | Percent Regeneration |
|---|---|---|
| 6 | 200 | 80.82 |
| 9 | 200 | 90.41 |
| 12 | 200 | 83.56 |
| 6 | 400 | 86.30 |
| 9 | 400 | 94.52 |
| 9 | 400 | 89.04 |
| 9 | 400 | 86.30 |
| 12 | 400 | 86.30 |
| 6 | 600 | 100.00 |
| 9 | 600 | 91.78 |
| 12 | 600 | 100.00 |

EXAMPLE III

A series of tests were run to determine the effect of various acids in adsorbed organolead chloride compounds from activated carbon.

In each test, activated carbon particles that contained 2.64 weight percent organolead chloride compounds were washed with 1:1 (by volume) nitric, hydrochloric, and acetic acid solutions. For each test, the carbon and the acid were placed in a flask and slowly stirred for one hour. At the end of this time, the acid was removed and fresh acid was added to the flask, again with stirring for 1 hour. A third acid wash was carried out in the same manner. Following the last washing, the acid was removed and the carbon was treated with distilled water until the pH of the effluent was the same as that of the feed. The results are in Table III below.

TABLE III

Effect of Various Acid Solutions in Removing Adsorbed Organolead Chloride Species on Activated Carbon

| Regeneration Method | Lead Content of Activated Carbon, Wt. % | % Lead Removal Basis Spent Carbon Before Treatment |
|---|---|---|
| HCl | 0.94 | 64.4 |
| $HNO_3$ | 0.10 | 96.2 |
| $CH_3COOH$ | 0.31 | 88.3 |

Thereafter, a series of tests were run to determine the effect of steam regeneration, using the method described in Example II hereinabove. The results shown in Table IV were obtained.

TABLE IV

Effect of Various Regeneration Methods in Removing Adsorbed Organolead Species on Activated Carbon

| Regeneration Method | Lead Content of Activated Carbon, Wt. % | % Lead Removal Basis Spent Carbon |
|---|---|---|
| HCl + 600° C. - Steam (4 hrs.) | 0.35 | 86.7 |
| $HNO_3$ + 600° C. - Steam (4 hrs.) | 0.07 | 97.3 |
| $CH_3COOH$ + 600° C. - Steam (4 hrs.) | 0.25 | 90.5 |

EXAMPLE IV

A series of tests were conducted to determine the effect of sodium chloride concentration on the removal of adsorbed organolead chloride species from activated carbon using aqueous sodium chloride.

In each test, 1-gram samples of activated carbon containing 5.85 weight percent adsorbed organolead chloride were stirred slowly in 100 milliliters of aqueous sodium hydroxide solution for 19 hours at room temperature. The carbon was then filtered from the solution. The solution was analyzed for dissolved lead.

The concentration of the caustic solutions was varied from 1.1 weight percent NaOH to 17.0 weight percent NaOH while the total volume of solution was the weight of carbon was kept constant. The results are summarized in Table V.

TABLE V

Removal of Lead From Spent Carbon by Aqueous Caustic Soda Solution

| Caustic Solution | | Lead Removed from Carbon Wt. % of Total Adsorbed Organdead Chlorides |
|---|---|---|
| Wt. % NaOH | NaOH/Pb, Moles | |
| 1.1 | 100 | 45 |
| 2.2 | 200 | 47 |
| 4.6 | 410 | 41 |
| 7.0 | 620 | 65 |
| 10.5 | 940 | 68 |
| 17.5 | 1560 | 61 |

While the invention has been described with reference to specific embodiments thereof, it is not to be so limited except in the claims appended hereto.

I claim:

1. In a method of recovering organolead chloride compounds having the formula $PbR_{4-x}Cl_x$, where R is chosen from the group consisting of aryl groups and alkyl groups having from 1 to 8 carbon atoms and $x$ is a number from 1 to 3, from an organolead chloride compound bearing aqueous solution containing from about 1 to about 20 parts per million of organolead chloride compounds, which method comprises passing the organolead chloride compound bearing aqueous solution through a bed of solid particle carbonaceous material, said carbonaceous material having a particle size range of 100 percent passing 8 mesh, substantially none passing 40 mesh, a surface area of from about 500 to about 1,600 square meters per gram, and a porosity of from about 0.80 to about 0.85, and withdrawing aqueous solution containing less than one part per million of organolead chloride compound, the improvement comprising passing the organolead chloride compound bearing aqueous solution through the bed of carbonaceous material until the carbonaceous material contains at least one weight percent organolead chloride compound, thereafter contacting the carbonaceous material with an aqueous extracting solution chosen from the group consisting of 0.1 to 5.0 normal solutions of $HNO_3$, $N_2SO_4$, $HClO_4$, $HMnO_4$, HCl, HBr, and HI, and recovering an aqueous solution containing in excess of 50 milligrams per liter of organolead chloride compounds.

2. The method of claim 1 comprising adjusting the pH of effluent from the bed to between pH = 6 and pH = 8 and thereafter resuming the flow or organolead chloride compound bearing solution through the bed.

3. The method of claim 1 comprising contacting the carbonaceous material with steam at a temperature of from about 400° to about 1,000° C. for from about 2 hours to about 48 hours.

4. In a process of recovering organolead chloride compounds having the formula $PbR_{4-x}Cl_x$ where R is chosen from the group consisting of aryl groups and alkyl groups having from 1 to 8 carbon atoms and $x$ is a number from 1 to 3, from an organolead chloride compound bearing aqueous solution containing from about 1 to about 20 parts per million of organolead chloride compounds, which method comprises passing the organolead chloride compound bearing aqueous solution through a bed of solid particulate carbonaceous material, said carbonaceous material having a particle size range of 100 percent passing 8 mesh, substantially none passing 40 mesh, a surface area of from about 500 to about 1,600 square meters per gram, and a porosity of from about 0.80 to about 0.85, and withdrawing aqueous solution containing less than one part per million of organolead chloride compound, the improvement comprising passing the organolead chloride compound bearing aqueous solution through the bed of carbonaceous material until the carbonaceous material contains at least one weight percent organolead chloride compound, thereafter contacting the carbonaceous material with an aqueous extracting solution chosen from the group consisting of 0.1 to 5.0 normal solutions of potassium hydroxide and sodium hydroxide, and recovering an aqueous solution containing in excess of 50 milligrams per liter of organolead chloride compounds.

5. The method of claim 4 comprising adjusting the pH of effluent from the bed to between pH = 6 and pH = 8 and resuming the flow of organolead chloride compound bearing aqueous solution to the bed.

6. The method of claim 4 comprising adjusting the pH of effluent from the bed to between pH = 6 and pH = 8 and resuming the flow of organolead chloride compounds from the bed.

7. In a method of recovering organolead chloride compounds having the formula $PbR_{4-x}Cl_x$, where R is chosen from the group consisting of alkyl groups having from 1 to 3 carbon atoms and $x$ is a number from 1 to 3, from an organolead chloride compound bearing aqueous solution containing from about 1 to about 20 parts per million of the organolead chloride, which method comprises passing the organolead chloride compound bearing aqueous solution through a bed of solid particulate carbonaceous material, said carbonaceous material having a particle size range of 100 percent passing 8 mesh, substantially none passing 40 mesh, a surface area of from about 500 to about 1,600 square meters per gram, and a porosity of from about 0.80 to about 0.85, and withdrawing aqueous solution containing less than one part per million of organolead chloride compound, the improvement comprising passing the organolead chloride compound bearing aqueous solution through the bed of carbonaceous material until the carbonaceous material contains at least one weight percent organolead chloride compound, thereafter contacting the carbonaceous material with an aqueous extracting solution chosen from the group consisting of 0.1 to 5.0 normal solutions of $HNO_3$, $HClO_4$, $HMnO_4$, HCl, HBr, and HI, recovering an aqueous solution containing in excess of 50 milligrams per liter of organolead chloride compounds, thereafter adjusting the pH of effluent from the bed to between pH = 6 And pH = 8, and resuming the flow of the organoleadchloride compound bearing aqueous solutin through the bed.

* * * * *

UNITED STATES PATENT AND TRADEMARK OFFICE
CERTIFICATE OF CORRECTION

PATENT NO. : 4,038,301
DATED : July 26, 1977
INVENTOR(S) : Jack M. Otto

It is certified that error appears in the above–identified patent and that said Letters Patent are hereby corrected as shown below:

Column 11, line 25, "$N_2SO_4$" should be --$H_2SO_4$--.

Column 11, line 30, "or" should be --of--.

Signed and Sealed this

Twenty-fifth Day of October 1977

[SEAL]

Attest:

RUTH C. MASON
*Attesting Officer*

LUTRELLE F. PARKER
*Acting Commissioner of Patents and Trademarks*